United States Patent [19]
Deweer et al.

[11] Patent Number: 6,100,073
[45] Date of Patent: Aug. 8, 2000

[54] **ACID-STABLE AND THERMO-STABLE ENZYMES DERIVED FROM *SULFOLOBUS* SPECIES**

[75] Inventors: Philippe Deweer, Aalst; Antione Amory, Rixensart, both of Belgium

[73] Assignee: Genencor International, Inc., Rochester, N.Y.

[21] Appl. No.: 08/765,939

[22] PCT Filed: Jul. 7, 1995

[86] PCT No.: PCT/EP95/02703

§ 371 Date: Sep. 29, 1997

§ 102(e) Date: Sep. 29, 1997

[87] PCT Pub. No.: WO96/02633

PCT Pub. Date: Feb. 1, 1996

[30] Foreign Application Priority Data

Jul. 14, 1994 [GB] United Kingdom .................. 9414224

[51] Int. Cl.$^7$ ............................ C12P 19/14; C12P 19/20; C12N 9/32; C12N 9/30
[52] U.S. Cl. .............................. 435/99; 435/96; 435/105; 435/202; 435/203; 435/204
[58] Field of Search ................................ 435/99, 105, 96, 435/202, 203, 204

[56] References Cited

U.S. PATENT DOCUMENTS

| | | |
|---|---|---|
| 3,912,950 | 10/1975 | Tada . |
| 4,600,693 | 7/1986 | Kindle et al. . |
| 4,689,297 | 8/1987 | Good et al. . |

FOREIGN PATENT DOCUMENTS

| | | |
|---|---|---|
| 131 253 | 1/1985 | European Pat. Off. . |
| 180 952 | 5/1986 | European Pat. Off. . |
| 258 050 | 3/1988 | European Pat. Off. . |
| 644 260 | 3/1995 | European Pat. Off. . |
| 90/11352 | 4/1990 | WIPO . |
| 90/11357 | 10/1990 | WIPO . |
| 92/19744 | 12/1992 | WIPO . |
| 94/13792 | 6/1994 | WIPO . |

OTHER PUBLICATIONS

Agric. Biol. Chem. 50(1): 21–31 (Kanno), 1986.
J. Bacteriol. 128(2): 515–521 (Buonocore et al), 1976.
Lama, et al, "Starch Conversion With Immobilized Thermophilic Archaebacterium *Sulfolobus Solfataricus* ," *Biotechnology Letters*, vol. 12: pp.431–432 (1990).
Lama, et al., "Thermostable Amyloytic Activity from *Sulofolbus Solfataricus* ," *Biotech Forum Europe*, vol. 8: pp.201–203 (1991).
Shetty and Allen, "An Acid–Stable, Thermostable Alpha–amylase For Starch Liquefaction," *Cereal Foods World*, vol. 33: pp.929–933 (1988).
Swallow, K.W., "Analysis of Quantitation of the Carbohydrates in Honey Using High–Performance Liquid Chromatography," *J. Agric. Food Chem.*, vol. 38: pp.1828–1832 (1990).

*Primary Examiner*—Francisco Prats

[57] ABSTRACT

Novel acid-stable and thermo-stable enzymes having α-1,4 hydrolytic activity and a α-1,6 hydrolytic activity which are derived from strains of the genus Sulfolobus. These enzymes are capable of expressing high levels of α-1,4 hydrolytic activity, including the maximum α-1,4 hydrolytic activity thereof, at highly acidic pHs of between about 2.5 and about 4.5. These α-amylases are further capable of expressing high levels of α-1,4 hydrolytic activity, including the maximum α-1,4 hydrolytic activity thereof, at high temperatures of between about 90° C. and about 120° C. Particularly disclosed herein are such enzymes which are derived from strains of the species *S. acidocaldarius* and, in particular, *Sulfolobus acidocaldarius* DSM 639. Modified starch degradation (liquefaction and saccharification) processes using these novel enzymes are also disclosed herein.

33 Claims, 5 Drawing Sheets

ACID-STABLE AND THERMO-STABLE ENZYMES DERIVED FROM *SULFOLOBUS* SPECIES

The present invention relates to novel acid-stable and thermo-stable enzymes having an α-1,4 hydrolytic activity and which are derived from strains of the genus Sulfolobus, and in particular strains of the species *Sulfolobus acidocaldarius*, and the use of these novel enzymes in starch degradation.

α-amylases (E.C. 3.2.1.1) are hydrolyzing enzymes having α-1,4 hydrolytic activity in starch, amylopectin and starch. These enzymes are utilized for a wide variety of industrial applications. Such industrial applications can require that the α-amylase used be highly acid-stable and/or highly thermo-stable.

An important industrial application for such acid-stable and thermo-stable enzymes having such α-1,4 hydrolytic activity (such as α-amylases) is the enzymatic degradation (hydrolysis) of starch for the production of sugars, such as glucose. Because starch is composed of glucose units joined by both α-1,4 and α-1,6 [inkages, to complete the hydrolysis thereof, the use of a number of enzymes with differing substrate specificities are required. This enzymatic degradation process involves two enzymatic steps: liquefaction and saccharification.

In liquefaction, typically starch granules are slurried in water in the presence of an α-amylase. This slurry is naturally acidic, able to have a pH of about 4.0. The slurried granules/α-amylase are then gelatinized with heat by passage through a jet cooker, which rapidly raises the temperature to about 105° C.–110° C. After a few minutes, the temperature of the slurry is then decreased to 90° C.–95° C. and held at that temperature for at least one hour.

The α-amylases conventionally-used in liquefaction are those derived from *B. licheniformis* and *B. stearothermophilus*. These α-amylases hydrolyze the starch and solubilize the dextrins, producing low viscosity hydrolysates suitable for further processing (in saccharification) to sugar syrups, such as glucose syrups. Unfortunately, the use of those α-amylases requires that two major adjustments be made in liquefaction.

The first adjustment necessary to permit use of the conventional α-amylases in liquefaction is to raise the pH of the naturally-acidic pH of the starch slurry from about 4.0 to between about 5.5 and about 6.5. Such an adjustment is necessary to permit the maximum enzymatic activity of the α-amylase to be expressed (indeed, the pH optimum of the α-amylase from *B. licheniformis* is about 6.0). Such an adjustment is also necessary for the enzyme since, in liquefaction conditions, that enzyme is relatively unstable in pHs lower than 6.

However, increasing the pH of the starch slurry in liquefaction has drawbacks. These drawbacks include an increase of color formation, the risk of generating filtration problems and the spontaneous formation of maltulose which, because it cannot be hydrolysed to dextrose in (subsequent) saccharification, leads to a loss in yield. Thus, while performing liquefaction at the higher pH is generally considered as advantageous for the α-amylase, it is nonetheless considered disadvantageous for the process.

The second adjustment necessary to permit use of the conventional α-amylases in liquefaction is the use of calcium ions to stabilize the enzyme. Indeed, the α-amnylase of *B. licheniformis* requires that at least fifty (50) ppm (parts per million) calcium be used for stabilization thereof in liquefaction conditions. As the calcium ion concentration is increased, the stability of the α-amylase is increased, thereby permitting the liquefaction medium to have a lower pH. Unfortunately, however, the presence of these calcium ions interferes with the refining step in the production of high fructose syrups. A low concentration of calcium ions in liquefaction is therefore preferred.

A further drawback presented by the use of the conventional α-amylases is that, at temperatures higher than about 110° C., in liquefaction conditions, the conventional α-amylases are denatured (destroyed). In this regard, conventional α-amylases limit the temperatures used in liquefaction to the range of between about 90 and about 110° C. However, the use, in liquefaction, of higher temperatures of (greater than about 100° C.) up to about 120° C. would allow the dissolved solids concentration to be increased.

In saccharification (the second step in the manufacture of dextrose syrups), maltodextiins obtained from liquefaction are converted into glucose by a fungal glucoamylase, such as those which are derived from strains of Aspergillus, such as Optidex R supplied by SOLVAY, and Rhizopus. It is important that sacchanfication be conducted under conditions of pH and temperature which are optimal for the glucoamylase used. It is further important that, during saccharification, the α-amylase used in liquefaction expresses a level of enzymatic activity which (by being so low) does not interfere with that process.

Since the pH optimum of conventionally-used glucoamylases, such as that derived from strains of Aspergillus, is highly acidic (around pH 4.0), saccharification is optimally performed under highly acidic conditions (pH of from 4.0 to 4.5). Furthermore, since the temperature optimum of the conventionally-used glucoamylases is about 60° C., saccharification is optimally performed at about 60° C. Thus, to obtain optimal conditions, the pH of the liquefied starch suspension once again needs to be adjusted, this time in order to redecrease the pH from around 6.0 to below 4.5 after liquefaction, with the temperature being established at about 60° C.

Unfortunately, such an additional pH adjustment results in an increase in the concentration of salts, including salts which may have to be added during liquefaction to stabilize the α-amylase, in the starch suspension being saccharified. This increase in the salt concentration increases, in turn, the ionic strength of the starch suspension. Such an increase in the ionic strength is undesirable in that it interferes with the subsequent refining during the manufacture of fructose syrups.

From the above, it can readily be seen that it would be desireable to eliminate the need for the intermediate pH adjustment in enzymatic liquefaction by the provision of an enzyme having α-1,4 hydrolytic activity in starch and which, in liquefaction conditions, is both acid-stable and capable of expressing the maximum α-1,4 hydrolytic activity thereof in highly-acidic pH, such as those encountered in liquefaction. It can also be seen that it would further be desireable for such an enzyme to also be, in liquefaction conditions, both thermostable and capable of expressing the maximum α-1,4 hydrolytic (enzymatic) activity thereof at temperatures, such as those which are encountered in liquefaction, and preferably, also those temperatures which are higher than the temperatures encountered in liquefaction. It can still further be seen that it would be still further advantageous for such an enzyme to, in liquefaction conditions, be capable of expressing the α-1,4 hydrolytic (enzymatic) activity thereof essentially independently of calcium ion concentration. Finally, it can yet further be seen that it would be still further desireable for such an enzyme to, in saccharification conditions (temperatures of about 60° C. and pH of about 3.5–4.5) express levels of α-1,4 hydrolytic (enzymatic) activity which (is so low that it) does not interfere with that sacharification process.

Finally, it can also be seen that the provision of such an enzyme would be useful for other applications where α-amylases are presently commonly used and/or in other applications where such enzymes having α-1,4 hydrolytic activity are not presently commonly-employed, but where such activity would nonetheless be desireable, especially where highly acidic pH and/or high temperature conditions are involved.

Despite the advantages that such an enzyme, would provide, especially in the production of sugars from starch, to the best of our knowledge, no such α-amylase has been previously identified, isolated and/or purified. This is despite the fact that strains of the genus Sulfolobus and, in particular, the strain from which the enzyme of the present invention is derived, Sulfolobus acidocaldarius DSM 639, have been known, deposited in an-approved culture collection and available to the general public for a number of years.

While α-amylases derived from other strains of Sulfolobus are known, these α-amylases are not known to possess the properties (especially the desired acid-stable properties) described above. An example of such other known α-amylases derived from other species of Sulfolobus include that α-amylase which is derived from the species Sulfolobus solfataricus (see Lama et al., Biotechnology Letters, 1990, 12: 431–432 and Lama et al., Biotech Forum Europe, 1991, 8:201–203). That α-amylase (which is very different from the α-amylase of the present invention) possesses an optimum pH of 5.5 and an optimum temperature of 70° C. Unfortunately, both of these properties would restrict the use of the α-amylases from such species of Sulfolobus, as they also restrict the use of the conventional α-amylases, in a number of industrial applications, including liquefaction in the enzymatic degradation starch to sugars.

Further problems presented by the use of the α-amylase derived from S. solfataricus in liquefaction is that it is produced intracellularly and that it catalyzes the synthesis of trehalose. In fact, we are not aware of any acid-stable α-amylases which are extracellularly-secreted by any species of Sulfolobus.

We are also aware of the existence of acid-stable α-amylases derived from strains of the genus Pyrococcus (International Patent Application WO 90/11357). Unfortunately, while the enzymatic activity of that α-amylase is essentially independent of calcium ions, it nonetheless has a maximum activity in the pH range of between 5.2 and 5.8 and in the temperature range of between 90 and 105° C. Thus, that enzyme would not function under its optimal conditions in a liquefaction process ran at the pH discussed above. Furthermore, that enzyme would not function under its optimal conditions in a liquefaction process ran at temperatures higher than the 95° C.–110° C. typically encountered in such processes.

Pullulanases (E.C. 3.2.1.41) are well-known hydrolyzing enzymes having α-1,6 hydrolytic activity in pullulan and starch. Pullulanases are also utilized for a wide variety of industrial applications, including saccharification. Unfortunately, the adjustment of the pH of the suspension (to that which is optimal for conventional glucoamylases) during saccharification results in a suspension having a pH which is below that which is optimal for conventional pullulanases (pH of about 6.0).

While the use of pullulanases in liquefaction would be desireable, conventional pululanases do not possess good enzymatic activity in the process conditions encountered in liquefaction, including the lower (naturally-occuring) pH's discussed above. Thus, pullulanases are not conventionally employed in liquefaction despite the desireability thereof.

Accordingly, it can be seen that it would be further advantageous to provide an enzyme having an α-1,6 hydrolytic activity in starch which is capable of expressing good (and preferably maximum) α-1,6 hydrolytic activity in starch in highly acidic pHs (and, preferably, in the range of between 2.5 and 4.5) in the temperatures that can be encountered in liquefaction (between about 90° C. and about 110° C.) and/or saccharification (about 60° C.), so as to be capable of expressing good α-1,6 hydrolytic (enzymatic) activity in such highly acidic pHs which can be encountered during liquefaction and/or saccharification.

Amylopullulanases are lesser-known hydrolyzing enzymes having α-1,4 hydrolyzing activity in amylose and starch as well as α-1,6 hydrolyzing activity in pullulan and starch. Amylopullulanases are known to be naturally-produced by species of the genra Bacillus, Thermus, Clostridium, Thermoanaerobium, Thermoanaerobacter, Pyrococcus and Thermococcus. However, we are not aware of any such amylopullulanase which is derived from any species or strain of the genus Sulfolobus.

Accordingly, it can still further be seen that it would be still further advantageous to provide an amylopullulanases having α-1,4 hydrolyzing activity in starch, as well as α-1,6 hydrolyzing activity in starch which amylopullulanase is capable of expressing good (and preferably maximum) α-1,4 hydrolytic activity and/or α-1,6 hydrolytic activity in starch in highly acidic pHs (and, preferably, in the range of between 2.5 and 4.5) in the temperatures that can be encountered in liquefaction (between about 90° C. and about 110° C.) and/or saccharification (about 60° C.), so as to be capable of expressing good α-1,4 hydrolytic activity and/or α-1,6 hydrolytic (enzymatic) activity in such highly acidic pHs, which can be encountered during liquefaction and/or saccharification.

It is a primary object of the present invention to provide an enzyme, and in particular, an enzyme having α-1,4 hydrolytic activity in starch, which is capable of hydrolyzing starch for the production of sugars, such as glucose, and which, in the temperatures that can be encountered in liquefaction (between about 90° C. and about 110° C.), is both acid-stable and has a pH optimum in the range of between 2.5 and 4.5, so as to be capable of expressing maximum α-1,4 hydrolytic (enzymatic) activity in such highly acidic pH, including pH which can be encountered during liquefaction.

It is another primary object of the present invention, to provide such an enzyme, and in particular, such an enzyme having α-1,4 hydrolytic activity in starch, which, at the pH that can be encountered in liquefaction, is also both thermo-stable and has a temperature optimum in the range of between about 90° C. and about 110° C., so as to be capable of expressing maximum α-1,4 hydrolytic (enzymatic) activity in such high temperatures, including those temperatures encountered during liquefaction.

It is stiLu another primary object of the present invention to provide such a starch-hydrolyzing enzyme, which, at the pH that can be encountered in liquefaction, is also both thermo-stable and has a temperature optimum at temperatures which are higher than those typically encountered during liquefaction (temperatures from between about 110° C. and about 120° C.), so as to be capable of expressing maximum α-1,4 hydrolytic (enzymatic) activity in such higher temperatures, so that the concentration of dissolved solids being liquefied may be increased.

It is still yet another object of the present invention to provide such a starch-hydrolyzing enzyme, and in particular such an enzyme having α-1,4 hydrolytic activity in starch, which, at the pH and temperatures that are typically encountered during saccharification (pH of between about 4.0 and about 4.5 and temperatures of about 60° C.), expresses a level of enzymatic activity which (is so low that it) does not interfere with that process.

A still yet further object of the present invention to provide such a starch-hydrolyzing enzyme, and in particular such an enzyme whose expression of α-1,4 hydrolytic (enzymatic) activity, in the conditions of pH and temperature which are typically encountered in liquefaction, is essentially independent of the presence of calcium ions, so that calcium ions need not be added during liquefaction, and further so that any calcium ions which may have been added do not reduce the ability of the enzyme to express the α-1,4 hydrolytic (enzymatic) activity thereof.

A further primary object of the present invention is to provide an enzyme having α-1,4 hydrolytic activity in starch which is both stable and capable of expressing high levels of α-1,4 hydrolytic (enzymatic) activity in highly-acidic pH and/or in high temperatures, so as to provide the long-sought means to eliminate the intermediate pH adjustment in enzymatic liquefaction which is necessary with the conventionally-used α-amylases.

A further object is to identify and provide such a starch-hydrolyzing enzyme, which is produced extracellularly.

A still further object is to provide such an enzyme which also has α-1,6 hydrolytic activity in starch.

In another aspect of the present invention, a further object is to provide an enzymatic composition, including the enzymes of the present invention, capable of hydrolyzing starch for the production of sugars, such as glucose.

In still another aspect of the present invention, a further primary object of the present invention is to provide an improved process for the liquefaction of starch with the aid of enzymatic hydrolysis, wherein liquefaction may be performed at the naturally-acidic pH of the slurry being liquefied, so that the need for intermediate pH adjustment of the said slurry is eliminated.

In yet another aspect of the present invention, a further primary object is to provide an improved process for the degradation of starch to sugars, such as glucose, in consecutive liquefaction and saccharification steps, wherein liquefaction is performed with an enzyme having α-1,4 hydrolytic activity in starch and without the necessity adjusting either the pH and/or the calcium ion concentration of either the starch slurry and/or the liquefied starch suspension during either liquefaction and/or saccharification to accommodate the said enzyme to the detriment of the process.

In this regard, it is yet a further object of the present invention to provide such a process for the liquefaction of starch, wherein liquefaction may be performed at temperatures being higher than the temperatures (90° C. to 110° C.) mentioned above, so that a higher dissolved solid concentration in the starch slurry to be liquefied may be provided.

It is another primary object of the present invention to provide such a process using an enzyme having α-1,4 hydrolytic activity in starch, which is capable of expressing high levels of α-1,4 hydrolytic (enzymatic) activity, and preferably the maximum α-1,4 hydrolytic (enzymatic) activity thereof, in the pH range and/or the temperature range which the starch slurry can encounter in liquefaction. In this manner, the necessity of either adjusting the pH and/or of adding calcium ions to the starch slurry is avoided, whereby the dissolved solids concentration of the liquefied starch suspension obtained therefrom is increased and further whereby interference with the subsequent refining step (for producing fructose syrups) due to the fact that the ionic strength of the obtained liquefied starch suspension is reduced and/or eliminated.

In accordance with the teachings of the present invention, disclosed herein are novel enzymes having α-1,4 hydrolytic activity in starch which are derived from species of the genus Sulfolobus including, in particular, the species *Sulfolobus acidocaldarius*. Specifically disclosed herein, as an example of such enzymes, is the enzyme having such α-1,4 hydrolytic activity which is derived from the strain *Sulfolobus acidocaldarius* DSM 639.

As used herein in referring to enzymes, nucleotides and microbial (i.e., Sulfolobus) strains, the term "derived from" means that the enzymes and nucleotides being spoken of are native to (originate from) the particular microbial strain from which they are said to be "derived from". In this regard, enzymes and nucleotides derived from *S. acidocaldarius* DSM 639 refer to those enzymes and nucleotides which are native to (originate from) *S. acidocaldarius* DSM 639. This defintion includes enzymes and nucleotide sequences which are identical to those enzymes and nucleotide sequences spoken of but which have (in the case of nucleotides) been either inserted into (used to transform) a suitable host organism, and (in the case of the enzyme) which has been secreted by a transformed host. This defintion also includes mutants, variants and derivatives of the enzymes and nucleotides referred to.

As used herein, the term "mutants and variants", when referring to enzymes, refers to enzymes obtained by alteration of the native (original) amino acid sequence and/or structure thereof by those means well known to those skilled in the art, such as by alteration of the DNA nucleotide sequence of the structural gene coding therefor and/or by direct substitution and or altering of the amino acid sequence and/or the structure of the enzyme.

As used herein, the term "mutants and variants", when referring to nucleotides refers to nucleotides and nucleotide sequences obtained by alteration of the native (original) state (nucleotides) and/or order (sequence) thereof by those means well known to those skilled in the art, such as UV and chemical mutagenesis.

As used herein, the term "mutants and variants", when referring to microbial strains (such as *S. acidocaldarius* DSM 639), refers to cells obtained by alteration of the DNA nucleotide sequence of, for example, the structural gene coding for the enzyme thereof having the α-1,4 hydrolytic activity.

The enzyme is a hydrolyzing enzyme capable of hydrolyzing starch for the production of sugars, such as glucose. It possesses extraordinary acidic and thermal stability as well as exhibiting favorable pH and temperature optima.

Preferably, this enzyme further has α-1,6 hydrolytic activity in starch.

As used herein, the term "α-1,4 hydrolytic activity" when referring to the enzyme of the present invention means that enzymatic activity resulting in the hydrolytic cleavage of the α-1,4 glycosidic bonds in starch and/or amylopectin and/or amylose.

As used herein, the term "α-1,6 hydrolytic activity" when referring to the enzyme of the present invention means that enzymatic activity resulting in the hydrolytic cleavage of the α-1,6 glycosidic bonds in starch and/or amylopectin and/or amylose.

In further accordance with the teachings of the present invention, there is disclosed herein a novel enzyme having α-1,4 hydrolytic activity in starch which, in temperatures of between about 90° C. and about 110° C. (the temperatures which can be encountered in liquefaction), is capable of expressing maximum α-1,4 hydrolytic (enzymatic) activity in highly acidic pH of between about 2.5 and about 4.5.

In this regard, use of the enzymes of the present invention would permit, in liquefaction, the long sought-after elimination of the intermediate pH adjustment of the slurry being liquefied which is required with the conventionally-used α-amylases.

Preferably, this enzyme further has α-1,6 hydrolytic activity in starch.

In still further accordance with the teachings of the present invention, this novel enzyme having α-1,4 hydrolytic activity in starch is further capable of expressing, in pH of between about pH 2.5 and about pH 4.5 (the pH which can be encountered in liquefaction), maximum α-1,4 hydrolytic (enzymatic) activity in high temperatures of between about 90° C. and 110° C.

In still further accordance with the teachings of the present invention, this novel enzyme is still further capable of expressing, in pH of between about pH 2.5 and about pH 4.5 (the pH which can be encountered in liquefaction), maximum α-1,4 hydrolytic (enzymatic) activity in temperatures of between about 110° C. and about 120° C. (temperatures which are typically higher than those which can be encountered in liquefaction).

In this regard, use of the enzyme of the present invention would, in the pH which can be encountered in liquefaction, permit liquefaction to be performed at temperatures that are higher than the temperatures mentioned above, so that a higher dissolved solid concentration in the starch slurry to be liquefied may be provided.

In still further accordance with the teachings of the present invention, this novel enzyme is, in pH of about 4.5 (pH which can be encountered in saccharification), capable of expressing a level of α-1,4 hydrolytic (enzymatic) activity in temperatures of about 60° C. (which temperatures are typically encountered during saccharification) that is so low that it does not interfere with that process.

It is further preferred that this enzyme be capable of expressing, in the pH and temperatures which can be encountered in liquefaction, an α-1,4 hydrolytic (enzymatic) activity either in the presence or in the absence of calcium ions in the starch slurry, such that the α-1,4 hydrolytic (enzymatic) activity of this enzyme during liquefaction be essentially independent of the calcium ion concentration of the starch slurry.

In still yet further accordance with the teachings of the present invention, there is disclosed herein an enzyme having α-1,4 hydrolytic activity in starch which are derived from a species of Sulfolobus, and which enzymes have an estimated molecular weight of about 95 kDa and/or an optimum pH of between about 3.0 and about 4.0 (about 3.5) and/or an optimum temperature of between about 110° C. and about 115° C.

Preferably, this enzyme further has an α-1,6 hydrolytic activity in starch.

In yet further accordance with the teachings of the present invention, disclosed herein are novel enzymes having α-1,4 hydrolytic activity in starch which enzyme is derived from species of the genus Sulfolobus, such as strains of the species *S. acidocaldarius*, (including, in particular *Sulfolobus acidocaldarius* DSM 639), which enzymes are capable of expressing the maximum α-1,4 hydrolytic (enzymatic) activity thereof in the pH range that can be encountered in liquefaction, such that the necessity of adjusting the pH of, and/or of increasing the calcium ion concentration of, the starch slurry during liquefaction is avoided. Preferably, this enzyme further has an α-1,6 hydrolytic activity in starch.

In still yet further accordance with the teachings of the present invention, disclosed herein are novel enzymes having α-1,4 hydrolytic activity in starch which are derived from species of the genus Sulfolobus, such as strains of the species *Sulfolobus acidocaldarius* (including, in particular, *Sulfolobus acidocaldarius* DSM 639), and which enzymes are capable of expressing the maximum α-1,4 hydrolytic (enzymatic) activity in the temperature range (between about 90° C. and about 110° C.) that can be encountered in liquefaction. Preferably, this enzyme further has an α-1,6 hydrolytic activity in starch.

In yet still further accordance with the teachings of the present invention, disclosed herein are novel enzymes having an α-1,4 hydrolytic activity in starch which are derived from species of the genus Sulfolobus, such as strains of the species *Sulfolobus acidocaldarius* (including, in particular, *Sulfolobus acidocaldarius* DSM 639), which enzymes are capable of expressing the maximum α-1,4 hydrolytic (enzymatic) activity thereof in both the pH ranges and the temperature ranges that can be encountered in the liquefaction step, such that the necessity of either adjusting the pH of, and/or of increasing the calcium ion concentration of, the starch slurry during liquefaction is avoided.

In another aspect of the present invention, disclosed herein is an enzymatic composition including the enzymes of the present invention having α-1,4 and/or α-1,6 hydrolytic activity in an appropriate carrier. Preferably, this composition is useful in the liquefaction of starch.

In another aspect of the present invention, disclosed herein is an improved process for the enzymatic liquefaction of starch, wherein such enzymatic liquefaction may be performed without any intermediate pH adjustment of the slurry being liquefied.

In still another aspect of the present invention, disclosed herein is an improved process for the degradation of starch to sugars, such as glucose, wherein such degradation is performed in consecutive liquefaction and saccharification steps without the necessity of adjusting the pH of the starch slurry during either liquefaction and/or saccharification.

In yet further accordance with the teachings of the present invention, disclosed herein is an improved process for the degradation of starch to sugars, such as glucose, wherein such degradation is performed in consecutive liquefaction and saccharification steps without the necessity of increasing (or otherwise adjusting) the calcium ion concentration of the starch slurry during either liquefaction and/or saccharification.

In yet still further accordance with the teachings of the present invention, disclosed herein is an improved process for the degradation of starch to sugars, such as glucose, wherein such degradation is performed in consecutive liquefaction and saccharification steps without the necessity of either adjusting the pH of, and/or increasing the calcium ion concentration of, the starch slurry during either liquefaction and/or saccharification.

In still further accordance with the teachings of the present invention, disclosed herein is an improved process for the enzymatic liquefaction of starch, wherein liquefaction may be performed at temperatures (of between about 110° C. and about 120° C.) being higher than those typically encountered (temperatures of 90–110° C.) in liquefaction, so that a higher dissolved solids concentration may be provided in the starch slurry to be liquefied.

These and other objects and advantages of the present invention will become apparent upon a reading of the following description, taken in conjunction with the following figures and examples.

Figure 1:
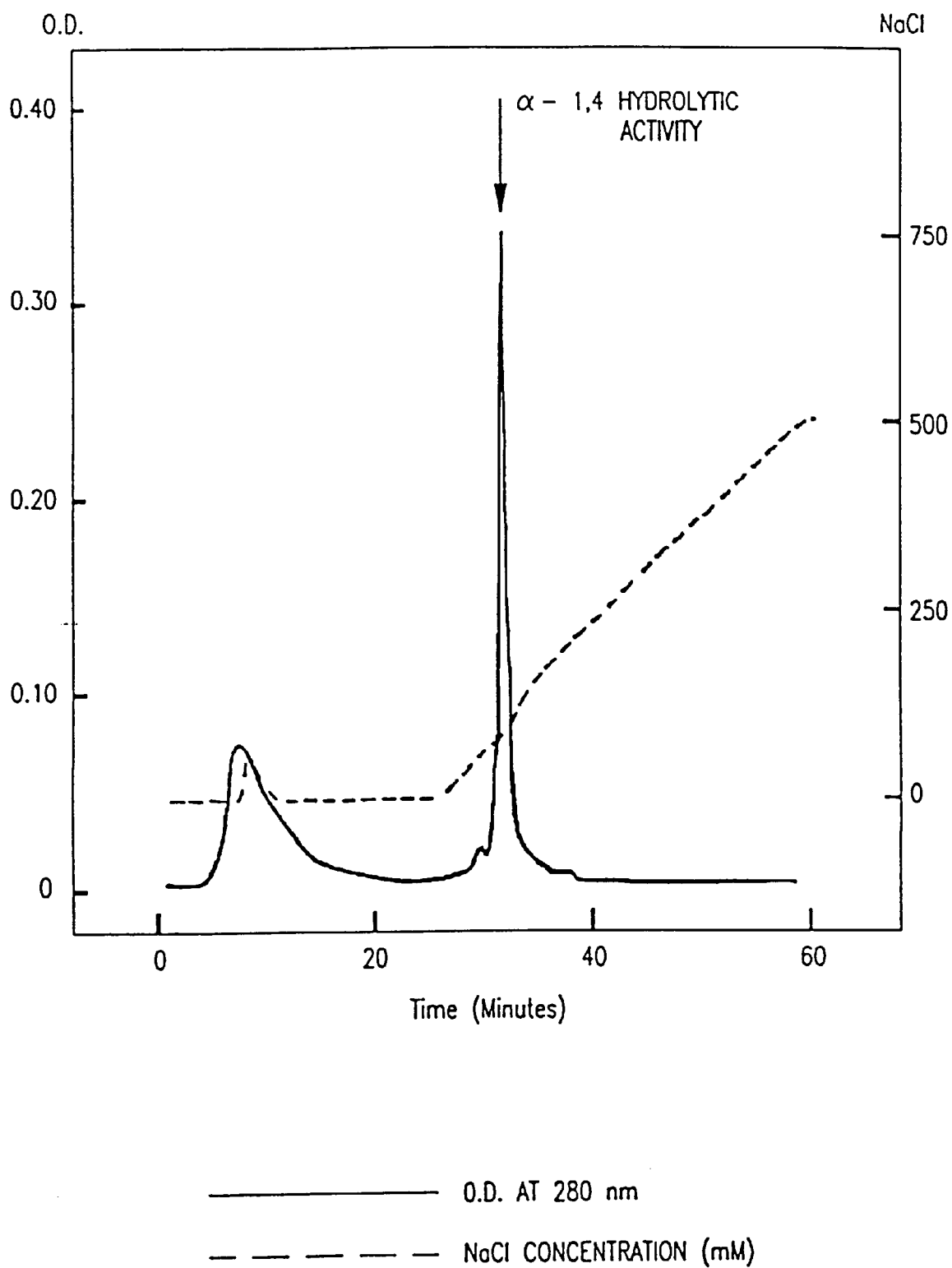
FIG. 1 is a chromatogram of the α-1,4 hydrolytic activity-containing fractions from Solution A.
Figure 2:
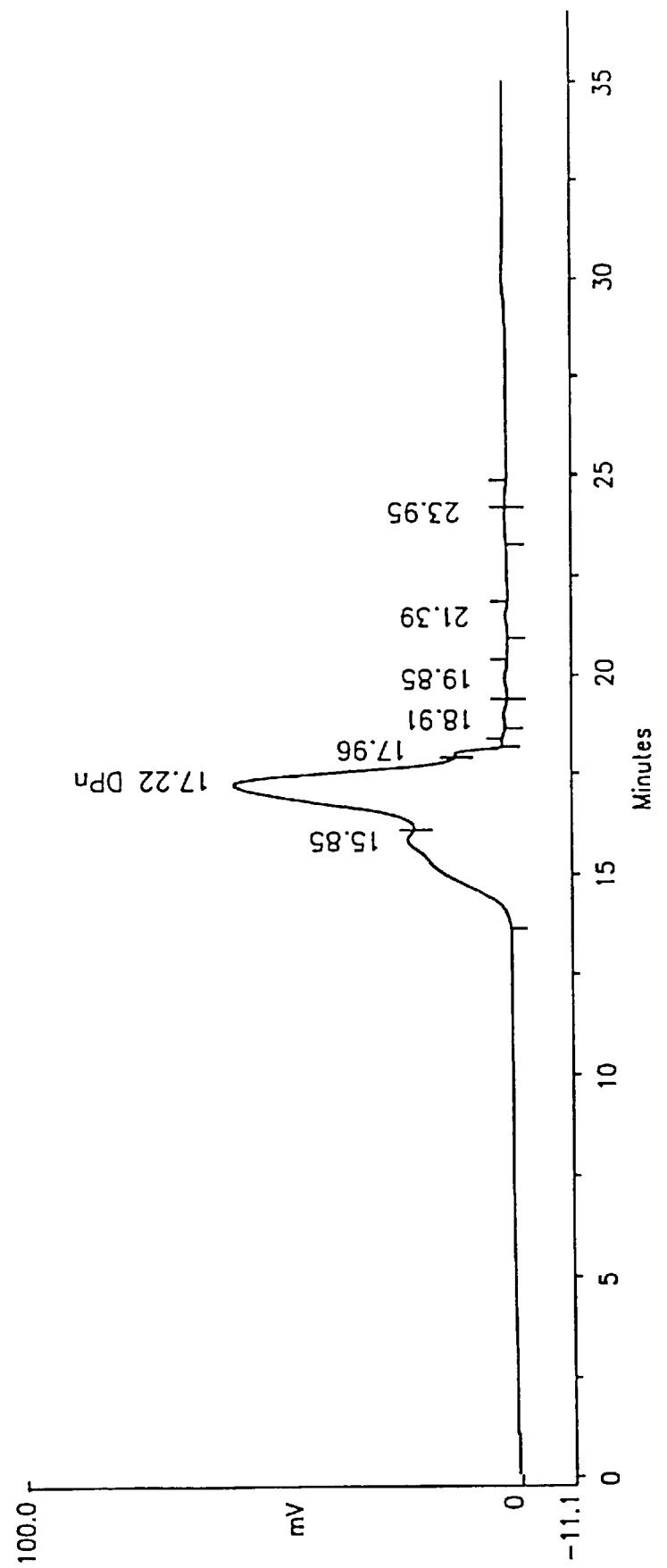
FIG. 2 is a chromatogram illustrating the distribution of oligosaccharides obtained from starch having been incubated for 20 hours in the absence of an enzyme (negative control).
Figure 3:
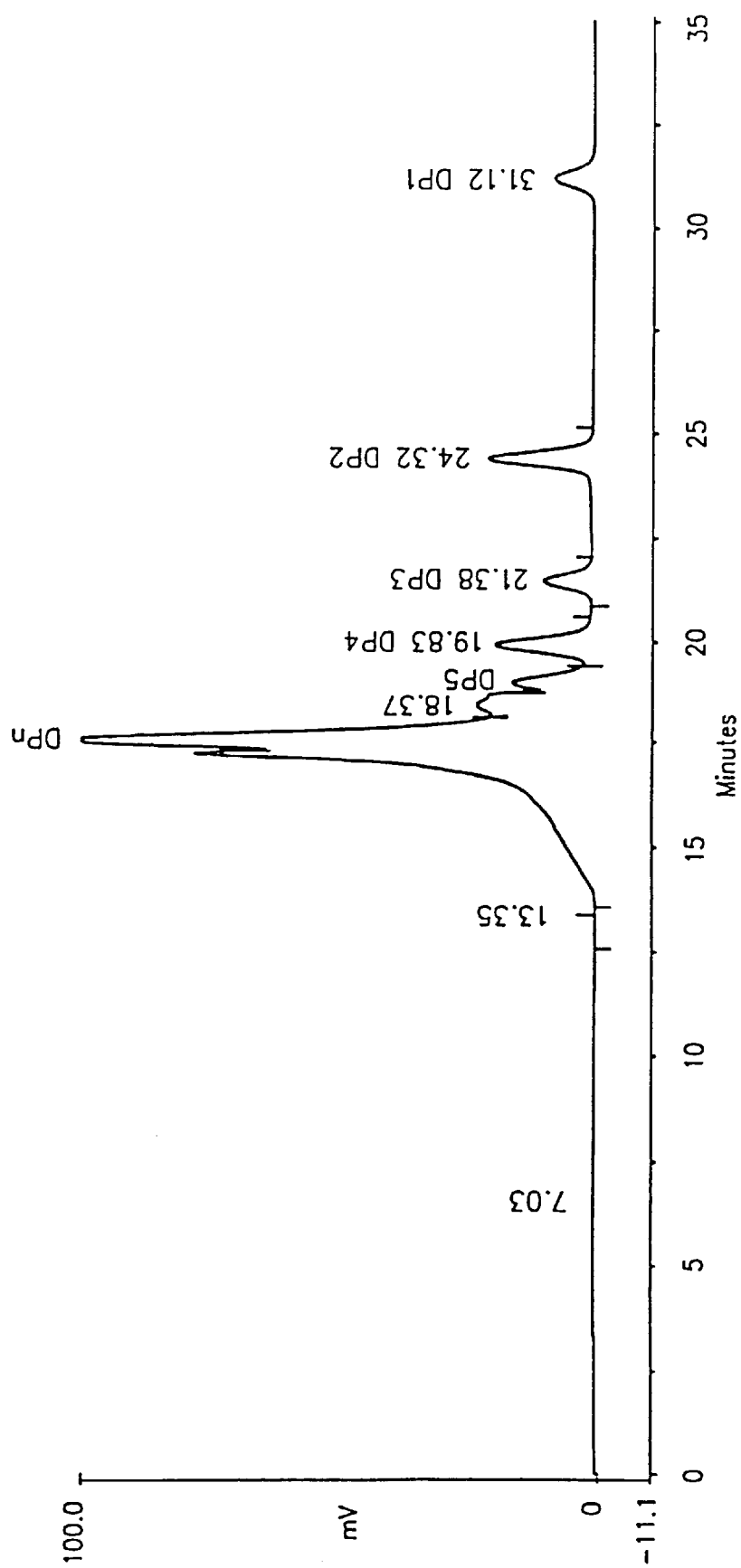
FIG. 3 is a chromatogram illustrating the distribution of oligosaccharides obtained from starch having been incubated for 1 hour with the enzyme of the present invention.
Figure 4:
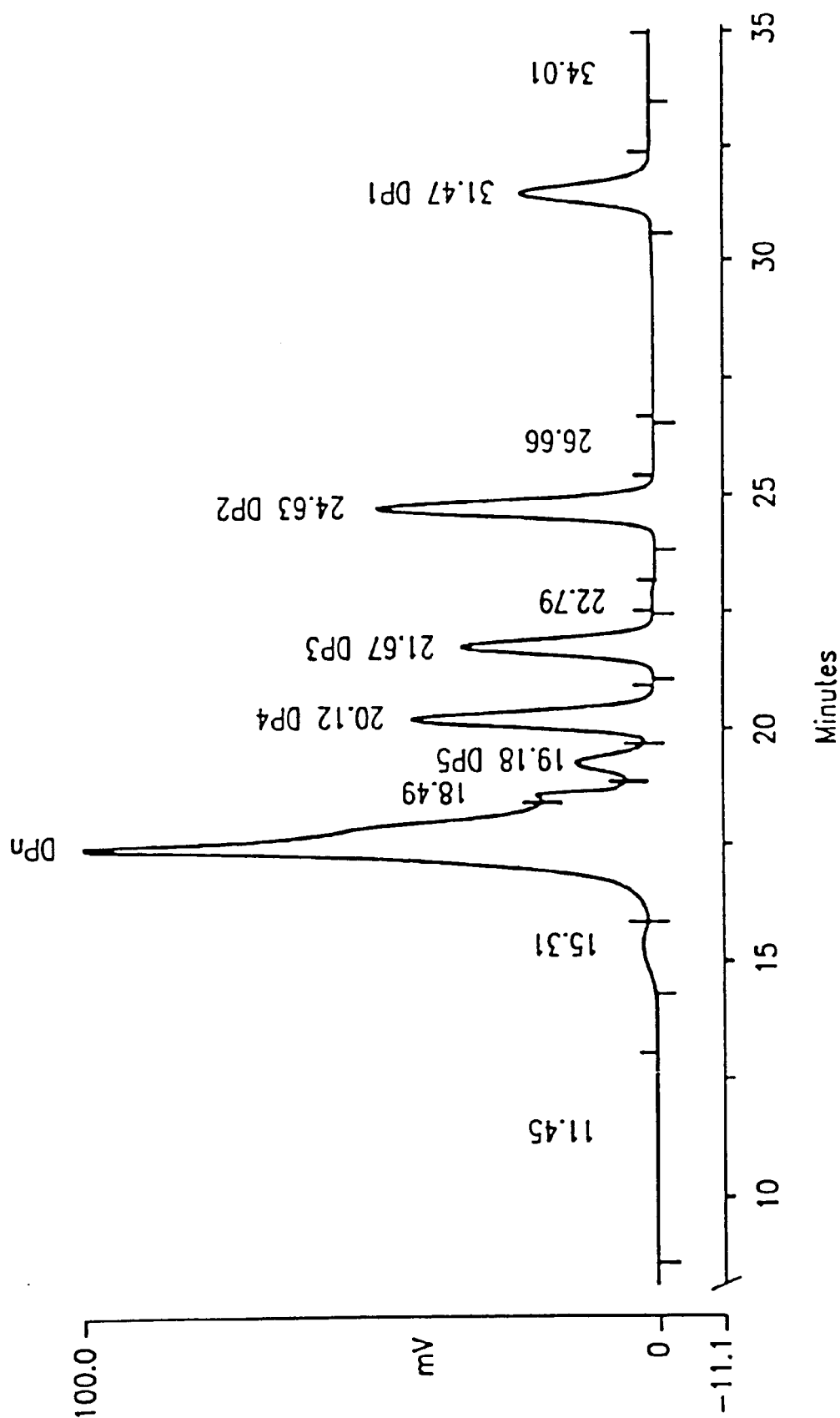
FIG. 4 is a chromatogram illustrating the distribution of oligosaccharides obtained from starch having been incubated for 5 hours with the enzyme of the present invention.
Figure 5:
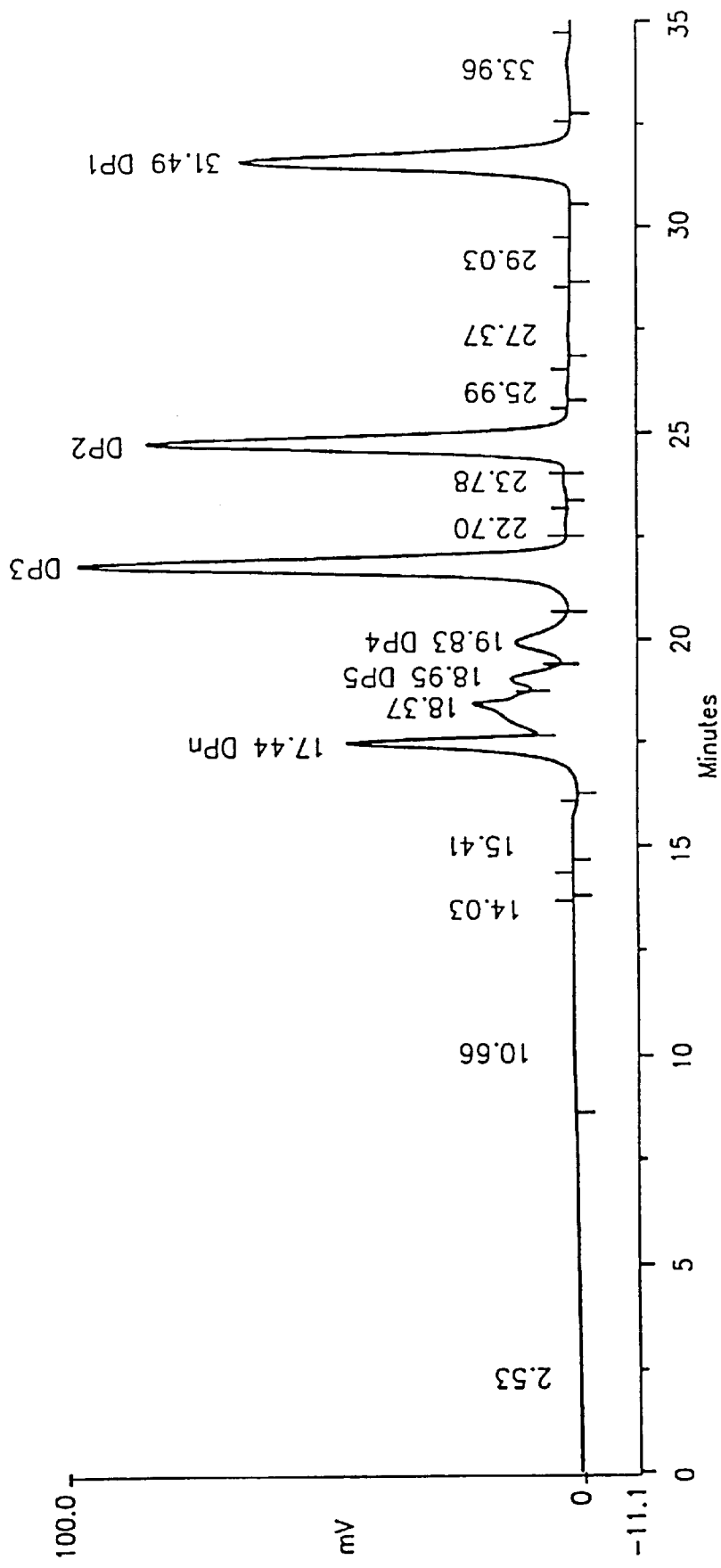
FIG. 5 is a chromatogram illustrating the distribution of oligosaccharides obtained from starch having been incubated for 20 hours with the enzyme of the present invention.

The hydrolyzing enzymes of the present invention are novel enzymes having α-1,4 hydrolytic activity in starch and α-1,6 hydrolytic activity in starch which are derived from strains (and natural isolates) of the genus Sulfolobus, such as strains of the species *S. acidocaldarius, S. brierleyi (Acidianus brierleyi), S. metallicus, S. shibatae* and *S. solfataricus*.

The enzymes of the present invention include that enzyme having α-1,4 hydrolytic activity in starch which is derived from the strain *Sulfolobus acidocaldarius* DSM 639.

The strain *Sulfolobus acidocaldarius* has been deposited in the Deutsche Sammlung von Mikroorganismen (DSM) located at Mascheroder Weg 1b Braunschweig, Federal Republic of Germany, under accession number DSM 639. This strain is publically-accessible.

These novel enzymes may also be derived from microbial strains which are able to grow under aerobic conditions at acidic pH of between about pH 3.0 and about pH 3.5 at about 75° C.

These enzymes are extracellularly secreted by the strains of the genus Sulfolobus (such as the strain *S. acidocaldarius* DSM 639 and other strains of *S. acidocaldarius, S. brierleyi, S. metallicus, S. shibatae* and *S. solfataricus*) into the fermentation broth.

These enzymes may be designated as EC 3.2.1.1 which are capable of hydrolyzing starch for the production of sugars, such as glucose.

Alternatively, these enzymes may be designated as E.C. 3.2.1.41, which are capable of hydrolyzing starch for the production of sugars, such as glucose. These enzymes may further be designated as "amylopullulanases" and/or pullulanases type (II).

These novel enzymes have an estimated molecular weight of about 95 kilodaltons (kDa's) as determined by an SDS-PAGE analysis method as defined in Example 3.

Particularly important properties of the enzymes of the present invention are their acid and thermal stability and their expression of high levels of α-1,4 hydrolytic (enzymatic) activity in high temperatures and/or highly-acidic pH. These properties are especially impressive in the pH and temperatures which can be encountered during liquefaction.

For purposes of illustration of the enzymes of the present invention, the properties thereof will be hereafter discussed by reference to those properties and characteristics of that enzyme derived from *S. acidocaldarius* DSM 639, which is believed to be representative of these acid and thermal stable enzymes having α-1,4 hydrolytic activity in starch which are disclosed herein that are naturally (extracellularly) secreted by other strains of the genus Sulfolobus, including other strains of the species *S. acidocaldarius*.

At about 110° C. (at about the upper range of temperatures which can presently be encountered in liquefaction), the novel enzymes of the present invention exhibit pH optima (for the α-1,4 hydrolytic activity thereof) at the extremely acidic pH of between about 2.5 and about 4.0 (which includes those pH which can be encountered in liquefaction), and more preferably from about 3.0 to about 3.5. At pHs as low as about 2.5, the enzymes of the present invention still exhibit (of the said α-1,4 hydrolytic activity) about 97% relative activity. Even at pH as low as about 2.0, these novel enzymes still exhibit considerable α-1,4 hydrolytic (enzymatic) activity (about 25% relative activity).

[As used herein, "Relative Activity" is that α-1,4 hydrolytic (enzymatic) activity as measured by the method as defined in Examples 4 and 5].

Further, and more importantly for the use of the enzymes of the present invention in liquefaction, at about 110° C., these enzymes exhibit about 95% relative activity (of α-1,4 hydrolytic activity) at pH of about 4.0 and about 84% relative activity (of α-1,4 hydrolytic activity) at pH of about 4.5. Indeed, and further demonstrating the flexibility of these enzymes, they still exhibit a substantial portion of their α-1,4 hydrolytic (enzymatic) activity (as used herein, "a substantial portion of their α-1,4 hydrolytic (enzymatic) activity" refers to a relative α-1,4 hydrolytic activity of at least about 50%) at pH as high as about 5.1.

At about pH 3.5, (at about the lower range of pH which can be encountered in liquefaction), the novel enzymes of the present invention exhibit temperature optima at the extremely high temperatures of from about 110° C. to about 115° C. (which includes those temperatures which can be encountered in liquefaction). At temperatures as low as about 90° C., these enzymes still exhibit about 48% relative (a-1,4 hydrolytic) activity. Even at temperatures as low as about 80° C., these novel enzymes still exhibit considerable α-1,4 hydrolytic (enzymatic) activity (about 28% relative activity).

Further, and more importantly for the use of the enzymes of the present invention in liquefaction, at about pH 3.5, it is noted that, in the temperatures which can be encountered in liquefaction (from about 90° C. to about 110° C.) the enzymes of the present invention express at least about fourty-eight percent (48%) of their maximum α-1,4 hydrolytic activity and are capable of expressing their maximum α-1,4 hydrolytic (enzymatic) activity. More specifically, in such conditions, these enzymes exhibit about 48% relative (α-1,4 hydrolytic) activity at about 90° C., about 81% relative (α-1,4 hydrolytic) activity at about 100° C., about 93% relative (α-1,4 hydrolytic) activity at about 105° C. and about 99% relative (α-1,4 hydrolytic) activity at about 110° C.

Also, at about pH 3.5 (in the pH which can be encountered during liquefaction), the enzymes of the present invention are further capable of expressing maximum α-1,4 hydrolytic (enzymatic) activity at high temperatures of between about 110° C. and about 120° C. In particular, at about 110° C. the enzymes of the present invention exhibit about 99% relative (α-1,4 hydrolytic) activity, at about 115° C. these enzymes exhibit about 100% relative (α-1,4 hydrolytic) activity and at about 120° C. these enzymes exhibit about 70% relative (α-1,4 hydrolytic) activity. As such, these novel enzymes are capable of expressing maximum α-1,4 hydrolytic (enzymatic) activity in temperatures that are higher than those temperatures which are commonly encountered in liquefaction with the use of the conventionally-used α-amylases. Such a high level of α-1,4 hydrolytic (enzymatic) expression at such high temperatures permits the starch slurry to be liquefied to have a higher dissolved solid concentration than is typically possible.

Finally, it is noted that, at about pH 3.5, the enzymes of the present invention are capable of expressing only about 5% relative (α-1,4 hydrolytic) activity at about 70° C. and about 4% relative (α-1,4 hydrolytic) activity at about 60° C. In this respect, at the temperatures and pH mentioned, these enzymes express levels of α-1,4 hydrolytic (enzymatic) activity which are so low (which are negligable) that they do not interfere with the enzymatic activity of saccharification. In this regard, the enzymes of the present invention is further adaptable for use in a continuous liquefaction/saccharification process.

It is further noted that the enzymes of the present invention are extremely stable in the highly acidic and high thermal conditions which can be encountered during liquefaction conditions. This stability is readily apparent not only in the presence of substrate (soluble maltodextrins), but also in the more demanding conditions where no substrate is present to protect the enzyme from the harsh conditions.

In particular, at about pH 3.5 and about 110° C. in the presence of a substrate (soluble maltodextrins), the enzymes disclosed herein have been determined to exhibit about 94% relative (α-1,4 hydrolytic) activity after about twenty minutes and about 91% relative (α-1,4 hydrolytic) activity after about thirty minutes. In these same conditions, these enzymes still exhibit about 74% relative (α-1,4 hydrolytic) activity after about 40 minutes and 70% relative (α-1,4 hydrolytic) activity after about fifty minutes. Indeed, these enzymes are so acid and thermal stable that they still exhibit about 72% relative (α-1,4 hydrolytic) activity after about sixty minutes in these same conditions.

The acid and thermal stability of the enzymes of the present invention are perhaps even more impressive when studied in the absence of a substrate which can protect the enzyme from those harsh acid and thermal conditions which can adversely affect its ability to express the α-1,4 hydrolytic (enzymatic) activity thereof. In this regard, it is noted that, at about pH 3.5 and about 110° C., in the absence of substrate, the enzymes disclosed herein still exhibit a substantial portion of their maximum α-1,4 hydrolytic (enzymatic) expression after about 30 minutes. In particular, these enzymes still exhibit about 79% relative (α-1,4 hydrolytic) activity after about 10 minutes, about 65% relative (α-1,4 hydrolytic) activity after 20 minutes and about 54% relative (α-1,4 hydrolytic) activity after about 30 minutes. It is further noted that the enzymes of the present invention still express an impressive level of α-1,4 hydrolytic (enzymatic) activity in such conditions even after about fifty minutes. In this regard, these enzymes still exhibit about 28% relative (α-1,4 hydrolytic) activity after about 40 minutes and about 22% relative (α-1,4 hydrolytic) activity after about fifty minutes.

In addition, during liquefaction, these enzymes are capable of expressing their α-1,4 hydrolytic (enzymatic) activity, essentially independently of the presence (or absence) of calcium ions in the starch slurry.

Finally, it is noted that these enzymes are capable of expressing the α-1,4 hydrolytic (enzymatic) activity thereof, during liquefaction, essentially independently of the presence of $Cu^{++}$, $Zn^{++}$, $Ni^{++}$, $Co^{++}$, $Ca^{++}$ and/or $Mg^{++}$. In this regard, it is noted that these cations exhibit only a negliable affect on the ability of the enzymes of the present invention to exhibit the α-1,4 hydrolytic (enzymatic) activity thereof and even then only in the presence of 10 mM of the cation. At concentrations less than about 10 mM, virtually no effect on the ability of the enzymes to exhibit the α-1,4 hydrolytic (enzymatic) activity thereof was observed.

Finally, it is noted that the enzymes of the present invention further have α-1,6 hydrolytic activity in starch. As such, it is a candidate for use in liquefaction and/or saccharification.

The enzymes of the present invention may be homologously expressed and extraceliularly secreted into the culture broth by strains of the genus Sulfolobus, such as *S. acidocaldarius* DSM 639, in their normal, native fashion.

The enzymes disclosed herein may also be obtainable with the use of recombinant DNA technology methods well-known to those skilled in the art, such as by isolating a DNA fragment encoding the enzyme; combining the DNA fragment with an appropriate expression signal in an appropriate plasmid vector; introducing the plasmid vector in an appropriate host (either as an autonomously replicating plasmid or integrated into the chromosome); cultivating the host organism under conditions leading to expression of the enzyme; and recovering the enzyme from the culture broth. Such techniques are described in Molecular Cloning, Laboratory Manual, (Sambrook, Fritsch, Maniatis) 2nd edition (1989) and Molecular Cloning, A Laboratory Manual. (Maniatis, T., Fritsch, E. F., and Sambrook, J.) Cold Spring Harbor Laboratory (1982).

Such recombinant expression may be homologous by another culture of the same strain of Sulfolobus (such as *S. acidocaldarius* DSM 639). Alternatively, such recombinant expression may be heterologous by another strain of the same species of Sulfolobus (such as another strain of *S. acidocaldarius*) and/or a strain a different species of the genus Sulfolobus (such as another strain of the species *S. Brierleyi, S. metallicus, S. shibatae* and *S. solfataricus*) and/or a strain of another genus entirely, such as strains of Bacillus (for example, strains of *Bacillus licheniformis, B. subtilis, B. alkalophilus, B. lentus, B. pumilus* and *B. Amyloliquefaciens*) and fungal strains, such as strains of Aspergillus (such as *Aspergillus niger*) and Rhizopus to name but two.

Regardless of which approach is taken, the enzymes from the various different hosts will have identical or partially identical immunochemical properties as can be determined immunologically by use of various well-known cross-reaction identity tests (see Axelsen, N. H., Handbook of Immunoprecipitation-in-Gel Techniques, Blackwell Scientific Publications (1983), Chapters 5 and 14).

For example, the immunological cross-reactivity of a variant of the enzyme of the present invention may be assayed using an antibody raised against or reactive with at least one epitope of the enzyme of the present invention which may be of a recombinant or native origin. The antibody, which may be either monoclonal or polyclonal, may be produced by methods well-known in the art, such as that described by Hudson, et al., 1989, Practical Immunology, Third Edition (1989), Blackwell Scientific Publications. The immunological cross-reactivity may be determined using assays known in the art, examples of which are Western Blotting or radial immunodiffusion assay, for example, as is described by Hudson supra.

The novel enzymes of the present invention may be produced by cultivation of strains of Sulfolobus (such as *S. acidocaldarius* DSM 639) under aerobic conditions in nutrient medium containing assimilable carbon and nitrogen together with other essential nutrient(s). The medium can be composed in accordance with principles well-known in the art.

During cultivation, the strains secrete the enzyme of the present invention extracellularly. This permits the isolation and purification (recovery) of the enzymes to be achieved by, for example, separation of cell mass from a culture broth (e.g. by filtration or centrifugation) while avoiding lysis. The resulting cell-free culture broth can be used as such or, if desired, may first be concentrated (e.g. by evaporation or ultrafiltration). If desired, the enzyme can then be separated from the cell-free broth and purified to the desired degree by conventional methods, e.g. by column chromatography, or even crystallized.

Preferably, the enzymes of the present invention may be isolated and purified from the culture broth into which they are extraceliularly secreted by: (1) concentration of the supernatant of the host culture; (2) passing the concentrated supernatant over an ion-exchange column; and (3) passing the concentrated supernatant over a hydrophobic interaction column.

The enzymes of the present invention may be formulated and utilized according to their intended application. In this respect, if being used in a detergent composition, the enzymes may be formulated, directly from the fermentation broth, as a coated solid using the procedure described in U.S. Pat. No. 4,689,297. Furthermore, if desired, the enzymes may be formulated in a liquid form with a suitable carrier. The enzymes may also be immobilized, if desired.

The enzymes of the present invention may be employed for various industrial applications, wherein amylotic activity in highly acidic and/or temperature conditions are involved. Such applications include those for which such activity is presently employed (for example, in liquefaction) or in processes wherein acidic α-amylases are not presently employed, but which could be advantageously modified as would be evident to one skilled in the art. Such processes range from those in the food industry (for example, baking), in the textile industry for the desizing of fibers, in alcohol fermentation (for brewery purposes and alcohol production). These enzymes may also be used in detergents, starch-based biodegradable plastics and in the synthesis of polysaccharides from glucose or oligosaccharides.

The enzymes of the present invention permit the use of processes for the degradation of starch to glucose in consecutive liquefaction and saccharification steps without the necessity of either adjusting the pH of, and/or increasing the calcium ion concentration of, the starch slurry/liquefied starch suspension during either liquefaction and/or saccharification.

In this respect, the enzymes of the present invention permit the implementation of a process for the degradation (hydrolysis) of starch into its degradation products, such as, for example, glucose, wherein neither the pH nor the calcium ion content of the starch slurry/liquefied starch suspension employed in either liquefaction and/or saccharification needs to be adjusted to accommodate the enzyme.

The enzymes of the present invention permit the implementation of a process for the degradation (hydrolysis) of starch to sugars, such as glucose, with the use of higher temperatures in liquefaction than those presently employed, such that the dissolved solids concentration of the starch slurry to be liquefied may be increased.

In the above fashion, the use of the enzymes of the present invention increases the efficiency of the glucose production achieved by the process of the present invention by eliminating the need to either adjust the pH of, and/or increase the calcium ion content of, the starch slurry employed in either liquefaction and/or saccharification, thereby increasing the efficiency of the process. Further, the use of these enzymes reduces costs by reducing the need for chemicals necessary to adjust the pH and/or calcium ion concentration of the starch slurry during either liquefaction and/or saccharification.

The present invention further relates to an improved process for the degradation (hydrolysis) of starch to sugars, such as glucose, in consecutive liquefaction and saccharification process steps without the necessity of either adjusting the pH of, and/or the calcium ion concentration of, the starch slurry during either liquefaction and/or saccharification.

The starch degradation process may be a standard liquefaction/saccharification process wherein starch granules are slurried with water in the presence of the enzyme, such as those processes described by Shetty and Allen in Cereal Foods World, 33:929–933 (1988). The pH of the slurry is naturally acidic, with pH of between about 3.5 and about 4.5 able to be encountered. The slurry granules are then gelatinized with heat by passage through a jet cooker, which rapidly raises the temperature of the slurry to between about 105° C. and about 110° C. The slurry is then held at that temperature for a few minutes before being decreased to between about 90° C. and about 95° C. The slurry is then held at that temperature for about one hour. While the pH may be adjusted and/or stabilizers (such as calcium ions) may be added to the slurry to stabilize the enzyme, it is noted that this entire liquefaction procedure may be conducted without any adjustment of the pH and/or addition of any calcium ions whatsoever. An example of such liquefactions such a jet-cooking process can be found by reference to U.S. Pat. No. 3,912,950.

Next, a fungal glucoa-mylase (derived from, for example, strains of Aspergillus) may be added to the liquified starch suspension. The temperature of the suspension is also reduced to about 60° C. The saccharification is then conducted (at pH of between about 4.0 and about 4.5). It is noted that this entire sacchanfication procedure may be conducted without any adjustment of the pH whatsoever. Examples of standard saccharification processes are described by Shetty and AMen in Cereal Foods World, 33:929–933 (1988).

If desired, the enzyme may also be used (for the α-1,6 hydrolytic activity) in saccharification.

The present invention further relates to an improved process for the degradation (hydrolysis) of starch to glucose, wherein liquefaction may be performed at temperatures being higher than those presently employed, such that the dissolved solids concentration of the starch slurry to be liquefied may be increased. In this regard, if desired, the heat cooker temperature of the slurry to be liquefied may be increased to between about 110° C. and about 120° C. at which temperature it is held for a few minutes before being decreased.

Dilutions, quantities, etc. which are expressed herein in terms of percentages are, unless otherwise specified, percentages given in terms of percent weight per volume (w/v). As used herein, dilutions, quantities, etc., which are expressed in terms of % (v/v), refer to percentage in terms of volume per volume.

Temperatures referred to herein are given in degrees centigrade (° C.).

Having thus described the enzymes of the present invention and the liquefaction and saccharification steps and other processes in which such enzymes may be employed, the following examples are now presented for the purposes of illustration and are neither meant to be, nor should they be, read as being restrictive.

EXAMPLE 1

Enzyme Production by *Sulfolobus acidocaldarius* DSM 639

A freeze-dried culture of *Sulfolobus acidocaldarius* DSM 639 was obtained from the Deutsche Sanmlung von Mikroorganismen (Germany), which had been deposited therein under accession number DSM 639.

A culture media was prepared containing the following ingredients:

| | |
|---|---|
| $KH_2PO_4$ | 2.0 mM |
| Maldex 15 (AMYLUM) | 0.2% (w/v) |
| $(NH_4)_2SO_4$ | 10.0 mM |
| Yeast extract (DIFCO) | 0.2% (w/v) |
| $MgSO_4.7H_2O$ | 1.0 mM |
| $CaCl_2.2H_2O$ | 0.5 mM |
| $FeCl_3.6H_2O$ | 0.07 mM |

The pH of this medium was then adjusted to 3.0 with $H_2SO_4$ and sterilized.

(The Maldex 15, a soluble maltodextrin substrate, was sterilized separately at neutral pH).

This freeze-dried culture was suspended in 1 ml of the culture medium.

Five (5) sterile 100 ml screw-cap bottles, each containing 40 ml of the culture medium were then inoculated with respective 200 µl quantities of the *S. acidocaldarius* DSM 639 culture suspension.

The inoculated, screw-cap bottles were then stored in a slanted position, in an incubator without agitation, for 2 days at 75° C.

The five samples were then used, in turn, to inoculate five (5) respective samples of 400 ml of medium located in respective one (1) liter screw-cap bottles.

The inoculated, 400 ml samples were then stored in a slanted position, in an incubator without agitation, for 2 days at 75° C.

The five (5) samples ogre then pooled, forming a single two (2) liter culture sample of *S. acidocaldarius* DSM 639.

Sixty more liters of the culture medium described above was then prepared and was placed in fermentor.

The fermentor was then inoculated with the two liter culture of *S. acidocaldarius* DSM 639, obtained as described above.

Fermentation of the culture in the 80 liter fermentor was conducted at 75° C., under constant stirring at 50 rpm. The air flow rate was 5 liters/minute (l/m), and the internal overpressure was maintained constant at 0.1 bar. After 90 hours of such cultivation, the fermentation broth was then cooled to room temperature.

The above fermentation results in, inter alia, the extracellular production of the enzyme of the present invention in the fermentation broth. The presence of such enzyme was then tested for by specifically assaying the fermentation broth for α-1,4 hydrolytic (enzymatic) activity, as is set forth below in Example 2.

EXAMPLE 2

Recovery and Purification of the Enzyme

The fermentation broth of the culture, obtained as described in Example 1, was then subjected to microfiltration using a Microgon KrosFlow II hollow fibers module (diameter 0.6 mm, 1 m², 0.22 micron) in order to remove biomass therefrom. This microfiltration produced 40 liters of a cell free solution.

A volume of 15 liters of demineralized water was then added to the retentate in three steps to wash the cells, yielding 55 liters of cell-free solution. This cell-free solution was then concentrated to 3 liters by ultrafiltration through an Amicon S10Y10 membrane. The concentrated solution was then subjected to a diafiltration step wherein a volume of 10 liters of sodium acetate buffer 5 mM (pH 3.5) was added to the concentrated solution in a stepwise fashion. The resulting solution was concentrated again to a final volume of 3 liters by ultrafiltration with the same Amicon S10Y10 membrane.

A subsequent concentration step was then carried out by ultrafiltration using cellulose acetate fibers SGI (1.5 m², 15 kD of cut-off), to a volume of 250 ml.

A still further concentration step was then carried out by ultrfltration using an Amicon YM10 membrane. This still further concentration resulted in obtaining a final 60 ml solution (solution A), containing the enzyme of the present invention.

A volume of 10 ml of solution A, obtained as described above, was applied at a flow rate of 5 ml/minute onto a Q-sepharose Hi-Load 16/10 (Pharmacies) column, previously equilibrated with a sodium acetate buffer 50 mM (pH 3.5). The column was eluted with a NaCl gradient from 0 to 500 mM. Fractions of 1 ml were collected, and the α-1,4 hydrolytic activity thereof was measured as described below. The fractions containing the α-1,4 hydrolytic activity were then pooled and a chromatogram performed (FIG. 1).

The purification was then repeated, as described above, with the remaining 50 ml of solution A (5×10 ml). All of the α-1,4 hydrolytic activity-containing fractions, from all the six independent column runs and purified in the same manner as described above, were then pooled, generating solution B.

The α-1,4 hydrolytic activity of the fractions obtained from the various purification steps are shown in Table 1, and were measured according to the following procedure.

In a hermetically sealed tube, 50 µl of the enzyme sample (or an appropriate dilution) were added to 250 µl of a solution containing 0.1% (w/v) Lintner'starch (Baker), citrate/phosphate buffer (100 mM/200 mM) at pH 3.5. The mixture was incubated for 15 minutes at 110±2° C. Incubation was then terminated by transferring the tube to an ice/water bath 0° C.).

A volume of 100 µl was then withdrawn from this mixture and added to 800 µl of a $I_2$/KI solution composed of 0.004% (w/v) $I_2$, 0.04% (w/v) KI, and HCl 0.25 M.

The absorbance was measured at 620 nm.

A blank was run by replacing the enzyme solution with water.

The activity in arbitrary units, was calculated as follows:

$$[(OD_b - OD_s)/OD_b] \times 100$$

in which $OD_b$ is the measured optical density of the blank, and $OD_s$ is the measured optical density of the sample.

TABLE 1

Purification of the Enzyme

| Steps | Volume (ml) | α-1,4 hydrolytic Activity (units/ml sample) | Yield (%) |
|---|---|---|---|
| Culture | 50,000 | 280 | 100 |
| Solution A (concentrate) | 60 | 82,000 | 35 |
| Solution B (after ion exchange) | 24 | 84,000 | 14 |

EXAMPLE 3

Molecular Weight Determination of the Enzyme by SDS-PAGE Analysis

A sample of the purified enzyme (Solution B), obtained as described above in Example 2, was then used for determination of the molecular weight by the use of SDS-PAGE analysis. This SDS-PAGE analysis was effectuated in denaturing conditions on polyacrylamide gel using Pharma PhastGel 10–15% (w/v) gels.

The sample was precipitated by the addition of trichloracetic acid [final concentration 10% (w/v)] and incubated for 1 hour at 0° C. The precipitated proteins were then collected by centrifugation at 10,000 g for 10 minutes. The resulting pellet was then dissolved in a sample buffer of 10 mM Tris/HCl (pH 8.0), 1 mM EDTA, 2.5% (w/v) sodium dodecyl sulfate (SDS), 5% (v/v) β-mercaptoethanol and 0.001% (w/v) bromophenol blue.

The resulting suspension was then denatured at 98° C. for 15 minutes. Insoluble materials were then removed by centrifugation at 10000 g for 5 minutes.

The resulting suspension was then analyzed by polyacrylamide gel electrophoresis (PAGE), Phast System purchased from Pharmacia LKB Biotechnology, under the conditions specified in, and following the procedures described by Pharmacia in the Separation Technque file N° 110 and using a polyacrylamide 10–15% gradient gel containing SDS (sodium dodecyl sulphate). The gels were run under standard conditions. The following Pharmacia LMW markers were used as molecular weight standards: phosphorylase b (canine muscle) 94 kDa; albumin (bovine serum) 67 kDa; ovalbumin (chicken egg white) 43 kDa; carboanhydrase (bovine erythrocytes) 30 kDa; trypsin inhibitor (soy bean) 20.1 kDa; and alpha lactalbumin (cow milk) 14.4 kDa.

After separation of the polypeptides, a Coomassie blue stainig of the gel was performed as described in the Development Technique File No. 200 from Pharmacia.

The results of the SDS-PAGE analysis revealed a single band of about 95 kilodaltons. Thus, the estimated molecular weight of this enzyme is determined to be approximately 95 kilodaltons (kDa's).

EXAMPLE 4

Measurement of Relative Activity of the Enzyme

1. Establishment of a Standard Curve

Since the correlation between the measured activity value $[(OD_b-OD_s)/OD_b]\times 100$, and the enzyme quantity was not linear, a standard curve was established in order to determine the relative α-1,4 hydrolytic (enzymatic) activity of the enzyme of the present invention.

Purified enzyme from solution B (obtained as described above in Example 2) was then obtained and diluted with water by a factor of 100, generating solution C.

A series of dilutions of solution C, containing the purified enzyme, were then prepared as are noted below in Table 2. It is noted here that the volumes (µl) indicated in Table 2 were diluted with water to a final volume of 200 µl.

An enzymatic assay was then performed using these various dilutions, according to the following procedure:

In respective hermetically-sealed tubes, 50 µl of the various diluted solutions C were added to 250 µl of a solution containing 0.1% (w/v) Lintner'starch (Baker) and citrate/phosphate buffer (100 mM/200 mM) at pH 3.5. The respective resulting mixtures were then incubated for 15 minutes at 110±2° C. Incubation was terminated by transferring the tubes to an ice/water bath (0° C.).

Respective volumes of 100 µl were withdrawn from each of these mixtures and then added to 800 µl of a $I_2$/KI solution composed of 0.004% (w/v) $I_2$, 0.04% (w/v) KI and HCl 0.25M. The absorbance was measured at 620 nm (Pharmacia LKB Ultraspec Plus). A blank was then run by replacing the enzyme solution by water. The value $[(OD_b-OD_s)/OD_b]\times 100$ was then calculated, and plotted versus the volume of solution C which was used in the dilutions. The 10 results are indicated below in Table 2.

TABLE 2

Standard Curve

| $\frac{(OD_b-OD_s)}{OD_b} \times 100$ | Volume (µl) of solution C used in the dilutions |
|---|---|
| 1.0 | 0 |
| 1.5 | 5 |
| 3.0 | 10 |
| 3.5 | 20 |
| 6.5 | 30 |
| 9.0 | 40 |
| 11.0 | 50 |
| 17.0 | 60 |
| 20.0 | 70 |
| 23.0 | 80 |
| 27.5 | 90 |
| 31.0 | 100 |
| 43.5 | 110 |
| 49.0 | 120 |

2. Standard Assay for Determination of the Relative Activity

In a hermetically sealed tube, 25 µl of solution C was mixed with 25 µl of water and then added to 250 µl of a solution containing 0.1% (w/v) Lintner'starch (Baker), citrate/phosphate buffer (100 mM/200 mM) at various pH values (as described in detail below). The mixture was then incubated for 15 minutes at various temperatures (see below). Incubation was terminated by transferring the tube to an ice/water bath (0° C.).

A volume of 100 µl was withdrawn from this mixture, and added to 800 µl of a $I_2$/KI solution composed of 0.004% (w/v) $I_2$, 0.04% (w/v) KI and HCl 0.25 M.

The absorbance was measured at 620 nm (Pharmacia LKB Ultraspec Plus).

A blank assay was performed by replacing the 50 µl enzyme solution C with water.

The relative activity (relative units) was calculated from the standard curve by calculation of the value $[(OD_b-OD_s)/OD_b]\times 100$, and then linearly extrapolating the corresponding volume (µl) from the two closest points of the standard curve.

The relative (α-1,4 hydrolytic) activity (%) is defined as the extrapolated volume value (µl), deduced from the standard curve.

EXAMPLE 5

Characterization of the Enzyme

1. Determination of Optimum pH

Respective samples of Solution C were obtained and prepared as described above in Example 4 to perform the standard assay.

The optimum pH of the enzyme of the present invention was then determined by running the standard assay described above in Example 4 on each of the tubes (samples) at a temperature of 110±2° C. and at various pH values ranging from 2.0 to 6.0. The results of such assays were then analyzed in the manner that was also described above in Example 4 for the standard assay.

The results of these assays are shown below in Table 3.

TABLE 3

| pH | Relative activity (%) |
|---|---|
| 2.0 | 25 |
| 2.5 | 97 |
| 3.0 | 99 |
| 3.5 | 100 |
| 4.0 | 95 |
| 4.5 | 84 |
| 5.1 | 50 |
| 5.6 | 7 |
| 6.1 | 1 |

According to the results of this assay, the optimum pH of the enzyme which is derived from *Sulfolobus acidocaldarius* DSM 639 (for the expression of the α-1,4 hydrolytic activity thereof) is about pH 3.5

2. Determination of the Optimum Temperature

Respective samples of Solution C were obtained and prepared as described above in Example 4 to perform the standard assay.

The optimum temperature of the enzyme derived from *Sulfolobus acidocaldarius* DSM 639 was determined by running the standard assay described above in Example 4 on each of the tubes (samples) at a constant pH of 3.5, and at various temperatures, ranging from 60 to 120° C. (±2° C.). The results of such assays were then analyzed in the manner that was also described above in Example 4 for the standard assay.

The results of this assay are shown below in Table 4.

TABLE 4

| Temperature (° C.) | Relative activity (%) |
|---|---|
| 60 | 4 |
| 70 | 5 |
| 80 | 28 |
| 90 | 48 |
| 100 | 81 |
| 105 | 93 |
| 110 | 99 |
| 115 | 100 |
| 120 | 70 |

According to this table, the optimum temperature of the enzyme derived from *Sulfolobus acidocaldarius* DSM 639 (for the expression of the α-1,4 hydrolytic activity thereof) is about 115° C.

3. Stability at 110° C. and pH 3.5

A volume of 10 μl of solution B obtained as described above in Example 2 containing the purified enzyme of the present invention was first diluted to 200 μl in citrate/phosphate 100 mM/200 mM buffer at pH 3.5, in the presence (or in the absence of 0.5% (w/v) Maldex 15 (Amylum), in hermetically sealed tubes. The tubes were then incubated at 110° C.±2° C. for various periods of time ranging from 0, 10, 20, 30, 40, 50, and 60 minutes.

After this incubation, the respective reaction mixtures were then diluted 5 times in water, and the α-1,4 hydrolytic (enzymatic) activities were measured under the standard conditions described above in Example 4.

The results are shown in Table 5.

TABLE 5

| Time | Relative activity (%) | |
|---|---|---|
| (minutes) | without substrate | with Maldex 15 |
| 0 | 100 | 100 |
| 10 | 79 | 94 |
| 20 | 65 | 94 |
| 30 | 54 | 91 |
| 40 | 28 | 74 |
| 50 | 22 | 70 |
| 60 | 8 | 72 |

According to Table 5, after incubation of the samples for 30 minutes at pH 3.5 and 110° C. without substrate, more than 50% of the α-1,4 hydrolytic activity is still present. A stabilistion effect by maltodextrins can also be observed.

4. Influence of Metal Cations and EDTA

Respective samples of Solution C were obtained and prepared as described above in Example 4 to perform the standard assay.

The influence of various metal cations and of EDTA on the α-1,4 hydrolytic activity of the enzyme derived from *Sulfolobus acidocaldarius* DSM 639 was determined by running the standard assay described above in Example 4 on each of the tubes (samples) in the presence of the additional various metal cations at a final concentration of 2, 5, and 10 mM. The results of such assays were then analyzed in the manner that was also described above in Example 4 for the standard assay.

The results of these Assays are showed in Table 6.

TABLE 6

| | Relative activity (%) | | | |
|---|---|---|---|---|
| added salt | 0 mM | 2 mM | 5 mM | 10 mM |
| $CaCl_2$ | 100 | 99 | 99 | 91 |
| $MgCl_2$ | 100 | 100 | 100 | 90 |
| $CuCl_2$ | 100 | 100 | 100 | 85 |
| $CoCl_2$ | 100 | 100 | 99 | 87 |
| $ZnCl_2$ | 100 | 100 | 99 | 89 |
| $NiCl_2$ | 100 | 100 | 100 | 82 |
| EDTA | 100 | 97 | 101 | 98 |

In the absence of calcium (with EDTA), the enzyme is fully active. No inhibition effect on α-1,4 hydrolytic activity was observed for the various added cations.

EXAMPLE 6

Small-Scale Starch Liquefaction

A staring volume of solution B, having the enzyme of the present invention, was obtained as described above in Example 2.

Solution B was then concentrated by acetone precipitation by adding acetone until a solution having a final concentration of 70% (v/v) acetone was obtained and the enzyme was permitted to precipitate out.

The resulting precipitated enzyme was collected by centrifugation at 4000 g for 15 minutes. The resulting pellet was recovered and dissolved in 20 mM sodium acetate buffer (pH 3.5) in half of the starting volume, to produce enzyme solution D, wherein the enzyme is concentrated by a factor of two.

α-amylases naturally-produced by a *B. licheniformis* [and sold under the trademark OPTTTHERM R LT420 by SOLVAY ENZYMES, Inc., USA)] and by a *B. stearothermophilius* [and sold under the trademark G-zyme R G995 by Enzyme Bio Systems)] were obtained and diluted, respectively, by factors of 1250 (v/v) and 1000 (v/v) with purified water generating, respectively, enzyme solutions E and F.

Starch slurries, which were buffered at various pH values enumerated in Table 7, were prepared as follows:

2 ml of 1 M acetic acid buffer (adjusted to the various pH values enumerated below in Table 7 with sodium hydroxide) was added to respective 3.3 gram samples of native corn starch (Meritena A from AMYLUM), and the respective final volumes thereof were adjusted to 7 ml with purified water.

Calcium chloride was then added to those slurry samples to be incubated with enzyme solutions E and F (as indicated in Table 7), to give a final calcium concentration of 0.75 mM (30 ppm calcium).

In respective hermetically-sealed tubes, respective 350 μl samples of the starch slurry were then combined with respective 150 μl samples of enzyme solutions D, E and F. Controls were carried out in the absence of enzyme were prepared by replacing the respective enzyme solutions with purified water.

The hermetically-sealed samples were then transferred to a thermostated glycerol-bath at 110° C., wherein they were vigorously agitated for 10 minutes. The temperature of the bath was then reduced to 95° C. while maintaining agitation and the incubation continued for another period of 80 minutes. Liquefaction was then terminated by transferring the tubes to a water bath at room temperature.

The respective liquefied reaction mixtures were then diluted with purified water by a factor of 40 (v/v).

A volume of 60 μl was then withdrawn from each sample and mixed with 3 ml of an an iodine solution having 0.004% $I_2$ (w/v), 0.04% KI (w/v) and HCl 0.25 M.

The optical densities of the resulting solutions were then measured at a wavelength of 620 nm, using the iodine solution as the blank reference.

The results are indicated below in Table 7.

TABLE 7

| pH | Solution D + 00 ppm Calcium | Solution E + 20 ppm Calcium | Solution F + 20 ppm Calcium |
| --- | --- | --- | --- |
| 6.0 | solid | 0.2 | 0.2 |
| 5.5 | solid | 0.5 | 0.3 |
| 5.0 | solid | 1.2 | 0.6 |
| 4.8 | n.d. | solid | solid |
| 4.0 | 0.7 | solid | solid |
| 3.5 | 0.5 | solid | solid | n.d.: Result Not Determined.

Negative controls which were run in the absence of enzyme remained solid at all pH values.

The above results demonstrate that the enzyme of the present invention is capable of liquefying starch under conditions of wherein there is a high dissolved solids concentration of about 33% (w/v) and high temperatures of 110° C. for primary liquefaction and 95° C. for secondary liquefaction.

EXAMPLE 7

Extensive Starch Hydrolysis

Liquefaction was conducted at 110° C. for various periods of time. The liquefaction mixtures were prepared by adding respective 150 μl samples of solution D (obtained as described above in Example 6) to respective 350 μl samples of starch slurries prepared as described above in Example 6 which had been buffered at pH 3.5 with a 1 M acetic acid buffer, as was also described above in Example 6, but without the addition of any calcium thereto. A negative control was prepared by replacing the enzyme solution with water for 20 hours of incubation.

The hermetically sealed samples were then transferred to a thermostated glycerol-bath at 110° C. and vigorously agitated for either 1, 5 or 20 hours as is noted below in Table 8. The incubations were terminated by transferring the tubes to a water bath as described above in Example 6. The iodine reactions were then measured as described above in Example 6. The results are indicated below in Table 8.

TABLE 8

| Time (Hours) | Optical Density |
| --- | --- |
| 1 | 0.8 |
| 5 | 0.3 |
| 20 | 0.0 |

These results demonstrate that the enzyme of the present invention is active and stable under liquefaction conditions at pH 3.5, even during incubation at 110° C. and, as such, is capable of extensive hydrolysis of starch under acidic conditions, making it a candidate for other applications, such as saccharification or the production of intermediate DE syrups.

EXAMPLE 8

HPLC Analaysis

The oligosaccharide compositions of the samples of Example 7 were then determined by HPLC using an Aminex HPX-87N resin in two 300 mm×7.8 mm (internal diameter) columns (BIORAD), which were eluted with purified water at 85° C. and a flow rate of 0.4 ml/min. Detection was carried out by measuring the refractive index. The HPLC chromatogram profiles obtained thereby can be seen by reference to FIGS. 2–5.

FIGS. 2–5 show that the major oligiosaccharides are formed after a prolonged hydrolysis of 20 hours are DP1, DP2 and DP3 (where DP is the degree of polymerization). After shorter incubation times, the chromatograms show the presence of various larger oligosaccharides (DP4, DP5 and DPn), but the smaller oligosaccharides (like DP1 and DP2) are already present, even at the earliest stage (1 hour). The DP4 oligosaccharide appears to be a transient product in that it accumulates at 1 and 5 hours and is then further degraded (possibly to DP1 and DP3) at 20 hours, indicating that the DP4 oligosaccharide is a substrate for the α-1,4 hydrolytic activity.

EXAMPLE 9

Hydrolysis of Pullulan

A pullulan solution was prepared which contained 3% (w/v) pullulan (SIGMA) and 200 mM acetic acid, adjusted to pH 3.5 with NaOH.

In respective hermetically-sealed tubes, respective 1 ml samples of the pullulan solution was mixed with respective 27 µl samples of enzyme solution D, obtained as described above in Example 6. The sealed tubes were then transferred for 6 hours to a glycerol bath thermostated at 110° C.

Incubation was terminated by transferring the tubes to a water bath at 0° C.

A negative control was run in parallel, under the same conditions, except that the enzyme solution D was replaced with purified water.

Samples were submitted to two separate HPLC analyses in order to determine the type of oligosaccharide formed after the hydrolysis of pullulan by the enzyme.

The first HPLC analysis to which the samples were submitted was a cation-exchange chromatography. This was achieved by serial-connecting two cation-exchange columns (ION 300 having a diameter of 300/7.8 mm followed by an HPX87H 300/7.8 mm column (BIORAD)], and protected by a precolumn (BIORAD). Elution was carried out at 60° C. with 10 mM $H_3PO_4$ at a flow rate of 0.4 ml/min. and the detection was performed by refractometry. The various peaks identified were quantified by directly comparing the peak areas HITACHI-MERCK D-6000 HPLC manager).

The results of the HPLC analysis is set forth below in Table 9.

TABLE 9

| Component | Retention Time (min) | Relative Quantity (%) |
|---|---|---|
| DP3 | 20.7 | 95 |
| DP2 | 23.6 | 3 |
| DP1 | 29.1 | 2 |

These results demonstrate that the major component generated by the hydrolysis of pullulan with the enzyme of the present invention is a DP3 oligosaccharide.

In order to determine the nature of the obtained DP3 oligosaccharide (maltotriose, panose or isopanose), a second HPLC analysis (an anion-exchange chromotography) of the sample obtained from the hydrolysis of pullulan by the enzyme of the present invention (as described above in this example) was then performed using a DIONEX CARBO-PAC PA1 10 µm 250/4 mm HPLC column, protected by a DIONEX precolumn.

Buffers A, B and C were prepared. Buffer A was prepared containing 100 mM NaOH. Buffer B was prepared containing 100 mM NaOH and 30 mM sodium acetate. Buffer C was prepared having 100 mM NaOH and 100 mM sodium acetate.

Elution was carried out at a flow rate of 0.7 ml/min with isocratic or linear gradients as follows:

The column was preequilibrated with Buffer A. From 0 to 4 minutes, a gradient of 0–100% of Buffer A was established. From 4 to 20 minutes, a gradient of 0–100% Buffer B was established. From 20 to 50 minutes, a gradient of Buffer C was established. From 50 to 60 minutes, an isocratic elution of 100% Buffer C was established. From 60 to 80 minutes, an isocratic elution of 100% Buffer A was established.

Elution was stopped at 80 minutes.

Detection was carried out by pulsed amperometry, under a 100 mV potential wherein maltotriose, panose and isopanose can be clearly separated. Maltose, panose and maltotriose standards were obtained from SIGMA. The value for the retention time of isopanose was extrapolated by reference to literature data (Swallow, K. W., J. Agric. Food Chem., 1990, 38:1828–1832) in which the same chromatographic system is employed.

Retention times were as follows: maltose 23.8 minutes; isopanose 28 minutes; panose 29.5 minutes; and maltotriose 31.3 minutes.

The HPLC analysis showed that the major DP3 oligosaccharide component obtained as described above exhibited a retention time of 31.28 minutes, thereby clearly identifying it as maltotriose and demonstrating the capability of the enzyme of the present invention to cleave α-1,6 glycosidic bonds.

Modifications may be made without departing from the basic spirit of the present invention. Accordingly, it will be appreciated by those skilled in the art that within the scope of the appended claims, the invention may be practiced other than has been specifically described herein.

What is claimed is:

1. An isolated enzyme comprising α-1,4 hydrolytic activity, characterized in that the enzyme is derived from a strain of the genus Sulfolobus and is capable, in pHs of 4.5 and below, of expressing the maximal α-1,4 hydrolytic activity thereof.

2. The isolated enzyme according to claim 1, further characterised by having a pH optima for the α-1,4 hydrolytic activity thereof of between about 3.0 and about 3.5.

3. The isolated enzyme according to claim 1, further characterised by having, at a pH of about 2.5, a relative activity being at least ninety-five per cent of the maximum α-1,4 hydrolytic activity thereof.

4. The isolated enzyme according to claim 1, further characterised by having, at a pH of about 4.5, a relative activity being at least eighty per cent of the maximum α-1,4 hydrolytic activity thereof.

5. The isolated enzyme according to claim 1, further characterised by having, at a pH of about 5.1, a relative activity being at least fifty per cent of the maximum α-1,4 hydrolytic activity thereof.

6. The isolated enzyme according to claim 1, further characterised by having, at a pH of between about 3.0 and about 3.5, a temperature optima for the α-1,4 hydrolytic activity thereof of between about 110° C. and about 115° C.

7. The isolated enzyme according to claim 1, further characterised by having, at a pH of about 3.5 and a temperature of about 90° C., a relative activity being at least fourty-five per cent of the maximum α-1,4 hydrolytic activity thereof.

8. The isolated enzyme according to claim 1, further characterised by having, at a pH of about 3.5 and a temperature of about 100° C., a relative activity being at least eighty per cent of the maximum α-1,4 hydrolytic activity thereof.

9. The isolated enzyme according to claim 1, further characterised by having, at a pH of about 3.5 and a temperature of about 120° C., a relative activity being at least seventy per cent of the maximum α-1,4 hydrolytic activity thereof.

10. The isolated enzyme according to claim 1, further characterised in that the enzyme has the capability of expressing the α-1,4 hydrolytic activity thereof essentially independently of the presence of calcium ions.

11. The isolated enzyme according to claim 1, further characterised in that the enzyme has the capability to express, after 60 minutes at about 110° C. and a pH of about 3.5 in the presence of a substrate, at least seventy per cent of the maximum α-1,4 hydrolytic activity thereof.

12. The isolated enzyme according to claim 1, further characterised in that the enzyme has the capability to express, after 60 minutes at about 110° C. and a pH of about 3.5 in the absence of a substrate, about twenty per cent of the maximum α-1,4 hydrolytic activity thereof.

13. The isolated enzyme according to claim 1, further characterised by further having α-1,6 hydrolytic activity.

14. An improved process for the hydrolysis of starch, wherein the improvement comprises providing an enzyme according to claim 1 and performing the hydrolysis without adjusting the pH of the starch slurry/liquefied starch suspension during liquefaction.

15. The improved process according to claim 14, wherein the hydrolysis is performed without adjusting the pH of the liquefied starch suspension during saccharification.

16. The improved process according to claim 15, wherein the hydrolysis is performed in consecutive liquefaction and saccharification steps without the necessity of adjusting the pH of the starch slurry/liquefied starch suspension.

17. The improved process according to claim 14, wherein the hydrolysis is performed without the necessity of increasing the calcium ion concentration of the starch slurry/liquefied starch suspension during liquefaction.

18. The improved process according to claim 14, wherein the hydrolysis is performed without the necessity of increasing the calcium ion concentration of the liquefied starch suspension during saccharification.

19. The improved process according to claim 14, wherein the hydrolysis is performed during liquefaction with a starch slurry/liquefied starch suspension having a pH of no greater than 5.

20. The improved process according to claim 19, wherein the pH of the starch slurry/liquefied starch suspension during liquefaction is no greater than 4.

21. The improved process according to claim 19, wherein the pH of the starch/liquefied starch suspension during liquefaction is no greater than 3.5.

22. The improved process according to claim 14, wherein the liquefaction is performed at temperatures of at least 110° C., so that a higher dissolved solids concentration is provided in the starch slurry being liquefied.

23. The improved process according to claim 22, wherein liquefaction is performed at approximately 120° C.

24. The improved process according to claim 22, wherein the pH of the starch slurry/liquefied starch suspension during liquefaction is no greater than about 5.

25. The improved process according to claim 24, wherein the pH of the starch slurry/liquefied starch suspension during liquefaction is no greater than about 4.

26. The improved process according to claim 25, wherein the pH of the starch slurry/liquefied starch suspension during liquefaction is no greater than about 3.5.

27. The isolated enzyme according to claim 1, wherein the enzyme is derived from a strain of the species *Sulfolobus acidocaldarius*.

28. The isolated enzyme according to claim 27, wherein the enzyme is derived from the strain *Sulfolobus acidocaldarius* DSM 639.

29. The isolated enzyme according to claim 1, wherein the enzyme is derived from strains of the species *S. brieleyi, S. metallicus, S. shibatae*, and *S. solfataricus*.

30. An enzymatic composition comprising an enzyme obtained from a strain of the genus Sulfolobus having α-1,4 hydrolytic activity wherein said enzyme is capable, in pHs of 4.5 and below, of expressing the maximal α-1,4 hydrolytic activity thereof.

31. The enzymatic composition according to claim 30, wherein the enzyme is derived from a strain of the species *Sulfolobus acidocaldarius*.

32. The enzymatic composition according to claim 31, wherein the enzyme is derived from the strain *Sulfolobus acidocaldarius* DSM 639.

33. An isolated enzyme comprising α-1,4 hydrolytic activity, wherein the enzyme is derived from a strain of the genus Sulfolobus, has an estimated molecular weight of about 95 kDa, and has an optimum pH of about 3.5 and an optimum temperature of 110–115° C. for the expression of α-1,4 hydrolytic activity thereof.

* * * * *